(12) United States Patent
Adamkiewicz

(10) Patent No.: US 7,056,278 B2
(45) Date of Patent: *Jun. 6, 2006

(54) METHOD OF TREATING OVERACTIVE BLADDER IN WOMEN

(75) Inventor: Maciej Adamkiewicz, Warsaw (PL)

(73) Assignee: ADAMED Sp. z.o.o., Czosnow (PL)

( * ) Notice: Subject to any disclaimer, the term of this patent is extended or adjusted under 35 U.S.C. 154(b) by 462 days.

This patent is subject to a terminal disclaimer.

(21) Appl. No.: 10/160,378

(22) Filed: May 30, 2002

(65) Prior Publication Data

US 2002/0179093 A1  Dec. 5, 2002

(30) Foreign Application Priority Data

Jun. 1, 2001 (PL) ...................................... 347843

(51) Int. Cl.
*A61F 2/02* (2006.01)
(52) U.S. Cl. .................. 600/30; 128/885; 128/DIG. 25
(58) Field of Classification Search ............ 600/29–32, 600/38, 41, 591; 128/830–835, 884, 885, 128/DIG. 25; 482/91, 148
See application file for complete search history.

(56) References Cited

U.S. PATENT DOCUMENTS 6,530,879 B1 *  3/2003  Adamkiewicz .............. 600/30

OTHER PUBLICATIONS

Martan et al, "Our preliminary experience with Kolpexin in the treatment of urinary stress incontinence", Sent. bl. Gynakol, 113:645-648, 1991. and translation.*

* cited by examiner

*Primary Examiner*—John P. Lacyk
(74) *Attorney, Agent, or Firm*—Darby & Darby

(57) ABSTRACT

A method of treating overactive bladder in women involves inserting an intravaginal device of substantially spherical shape and a diameter that fits the width of the vagina into the vagina above the levator ani muscle, and maintaining said device in the appropriate location inside the vagina for an extended period of time to exert its therapeutic effect. The method may further comprise performing pelvic floor exercises, preferably exercises consisting of contracting the levator ani muscle and squeezing soft objects between the knees while in a prone position, preferably twice a day, with said device left inside the vagina.

19 Claims, 3 Drawing Sheets

METHOD OF TREATING OVERACTIVE BLADDER IN WOMEN

FIELD OF THE INVENTION

The present invention relates to the method of treating overactive bladder in women.

BACKGROUND ART

Overactive bladder can occur in both men and women. It is a condition characterised by involuntary detrusor muscle contractions during the phase of urine collection in the bladder, which contractions may be spontaneous or provoked and can not be controlled by a person. Clinical manifestations of overactive bladder are: urinary frequency, nocturia, urinary urgency and/or urinary urge incontinence. These symptoms may occur separately or in conjunction.

Urinary frequency is defined by most authors as voiding more than 8 times per day, nocturia as the need to void during the night, between midnight and 6 am. Increased urinary urgency is defined as the number of urge episodes per month or per day and the length of time that the urge to void can be overcome before emptying the bladder. The most extreme form of urinary urgency is urinary urge incontinence, which results in episodes of urinary incontinence due to the inability to reach a toilet in time.

Current medical treatment in cases where a symptom or symptoms of overactive bladder are present involves administration of pharmacological agents.

Known methods of pharmacological treatment of overactive bladder involve administering anticholinergic agents, for example such as oxybutynin, tolterodine etc. (see e.g. Patent Specification EP325571B1, 1991), scopolamine and propantheline (see: J. P. Weiss and J. G. Blaivas, Nocturia, J. Urol. 163, 5–12 (2000). Anticholinergic agents suppress detrusor activity and inhibit normal voiding by blocking the parasympathetic system. They also show systemic activity, again by acting on the parasympathetic system, which results in side effects, including mucosal dryness, reduction in gastric secretion within the gastrointestinal tract and suppression of intestinal motility.

Aside from adverse effects, there are numerous contraindications to treatment using anticholinergic agents, such as glaucoma, cardiac arrhythmia and urinary retention.

Estrogen supplementation, pelvic floor exercises and behavioural exercises, such as voiding at certain specified times, also play a role in alleviating symptoms of overactive bladder.

The object of this invention is to provide a method of treating overactive bladder in women without the adverse effects associated with the pharmacological treatment mentioned above and to improve the quality of life of women affected by this condition.

DESCRIPTION OF THE INVENTION

Surprisingly, it has been found that disadvantages associated with pharmacological treatment could be avoided by treating overactive bladder in women with a suitable intravaginal device.

In the first aspect the invention relates to a method of treating overactive bladder in women, which comprises inserting an intravaginal device of substantially spherical shape and a diameter that fits the width of the vagina, into the vagina above the levator ani muscle, and maintaining said device in the appropriate location inside the vagina for an extended period of time to exert its therapeutic effect.

Said method may further comprise performing pelvic floor exercises, consisting in contracting the levator ani muscle and squeezing soft objects placed between the knees while in a prone position, preferably twice a day, with said device left inside the vagina. Such exercises may strengthen appropriate muscles and narrow the width of the vagina.

Accordingly, said method may also comprise replacing said device with another substantially spherical device of a smaller diameter, after strengthening of appropriate muscles and narrowing the width of the vagina.

Furthermore, the method of the above first aspect of the invention may optionally comprise administering pharmacological agents, typically used in the treatment of overactive bladder, particularly anticholinergic agents, for example such as mentioned above.

According to the second aspect of the invention there is provided a method of treating overactive bladder in women, which comprises the following steps:

providing a first set of at least two intravaginal devices of substantially spherical shape and different diameters (the therapeutic set), designed to be inserted into the vagina and to be left in the location above the levator ani muscle where said device exerts its therapeutic effect, and providing a subset of at least two measuring intravaginal devices (the measuring subset) of substantially spherical shape and different diameters, said diameters corresponding to the diameters of the devices of the first set, each of said measuring devices having a measuring scale strip attached thereto to determine the location of the device in the vagina;

determining the size and location of said device of the first set to be left in the body, by placing a measuring device of said subset such that the diameter of said measuring device fits the width of the vagina, in the appropriate location in the vagina;

removing said measuring device of said subset from the vagina, and inserting a device of substantially spherical shape having the same diameter as that of the removed measuring device of the subset, into the vagina.

Preferably, the method as defined above comprises further step of:

removing said device of said first set from the vagina after a period of time and replacing it with another device of said first set of smaller diameter.

Preferably, the following step is included before replacing step as defined above:

determining the appropriate size and location of said device of said first set to be left in the body, by placing measuring device of a smaller diameter of said subset in the appropriate location in the vagina.

Furthermore, the method of the second aspect of the invention may optionally comprise performing pelvic floor exercises, consisting in contracting the levator ani muscle and squeezing soft objects placed between the knees while in a prone position, preferably twice a day, with said device of said first set remaining inside the vagina. Such exercises may strengthen appropriate muscles and narrow the width of the vagina.

Furthermore, this method may optionally comprise administering pharmacological agents, typically used in the treatment of overactive bladder, particularly anticholinergic agents, for example such as mentioned above.

The phrase "an intravaginal device of substantially spherical shape" is intended to include both regular spheres and symmetrical spheroidal solids deviating from a spherical shape, for example spheroids, such as a "flattened" spheroid. Preferably, regular spheres (i.e. balls) are used.

Preferably in the methods according to both aspects of the invention the devices as light as possible are used, so that they exert their effect through their shape rather than through their weight. Devices may be solid, made, for example of from light and/or cellular plastics, or they may be hollow. Most preferably, the device is hollow.

Devices of substantially spherical shape according to the first aspect of the invention, as well as devices from the first set and the measuring subset according to the second aspect of the invention may be made of metal or plastic suitable for medical applications, such as methyl polimetacrylate or policarbonates. In a preferred embodiment the therapeutic device is fitted with a loosely hanging thread that facilitates its removal.

The methods according to both aspects of the invention may be used to treat symptoms of overactive bladder, such as urinary frequency, nocturia, urinary urgency and/or urinary urge incontinence, occurring separately or in conjunction.

The invention will be described in more detail with reference to the enclosed drawings, wherein:

FIG. 1. shows a set of therapeutic devices (balls). Ball (1) is fitted with a thread (2) for removing it from the vagina.

FIG. 2. shows a subset of spherical measuring devices. The measuring device (3) is fitted with a measuring scale strip (4).

In FIGS. 3A, 3B, 4A and 4B (7) indicates the anus, (8) indicates the bladder and (10) indicates the uterus.

Figure 1:
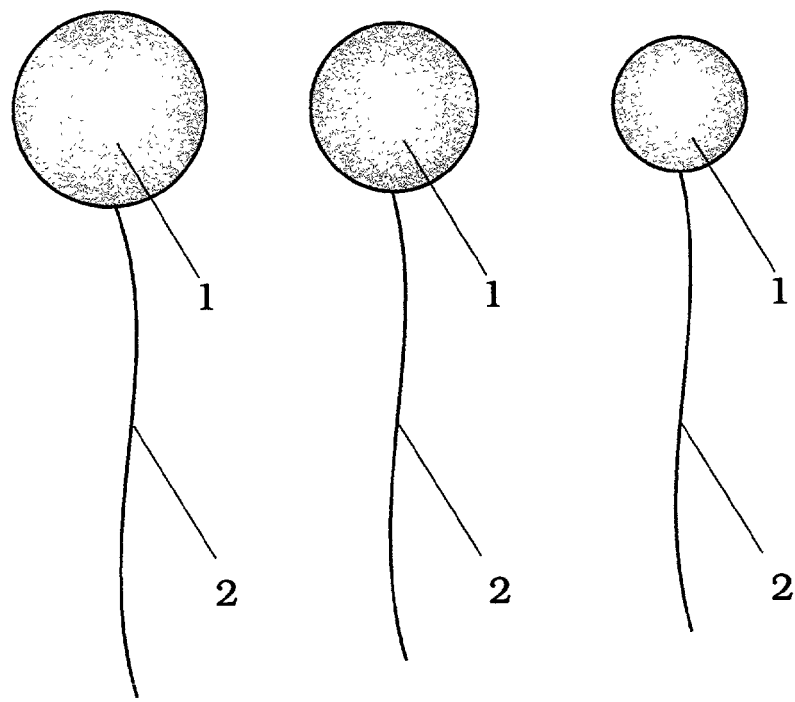
Figure 2:
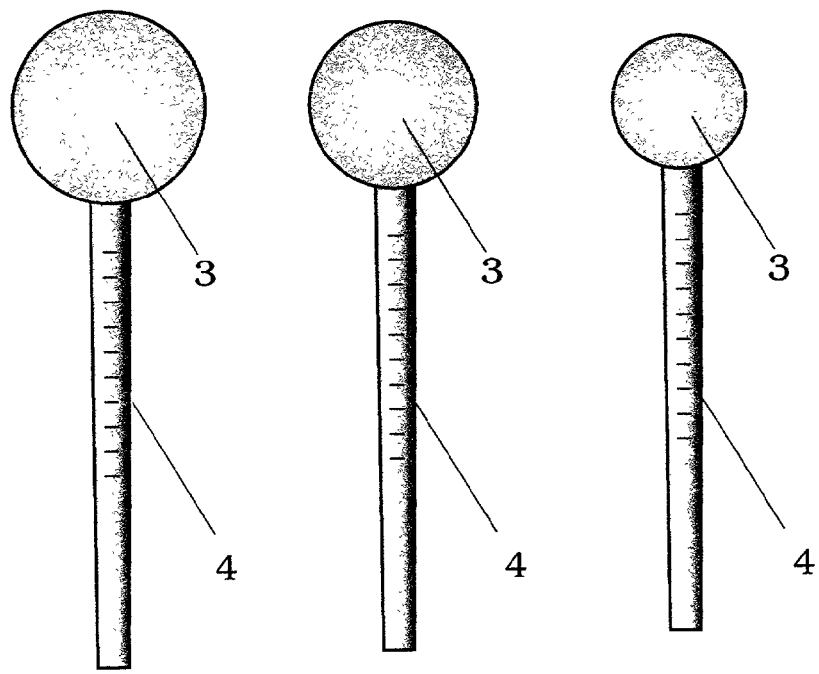

The set as shown in FIGS. 1 and 2 is described in detail in the published European Patent Application No. EP 0955024A2 and in the corresponding USA Patent Specification (U.S. application Ser. No. 09/303981 dated May 4, 1999), now U.S. Pat. No. 6,530,879 granted Mar. 11, 2003, which are included in their entirety to this application by way of reference. In the above publications it is stated that the set is useful for the treatment of urogenital prolapse and urinary stress incontinence.

Treatment of symptoms of overactive bladder is performed in practice by placing the intravaginal vaginal device (1) of a diameter selected so that it fits the vagina, into the vagina (5) of a woman with overactive bladder above the levator ani muscle (6). The selection of the appropriate device size (diameter), determining its appropriate location inside the vagina and determining if and when the device must be replaced by a smaller one may be made by skilled medical practitioner.

Selection of the appropriate device diameter to fit a woman's vagina involves choosing such a diameter that will result in the device (1) modelling the posterior wall of the urinary bladder (9) without stretching the vaginal walls, and remaining in place above the crura of the levator ani muscle (6).

Figure 3A:
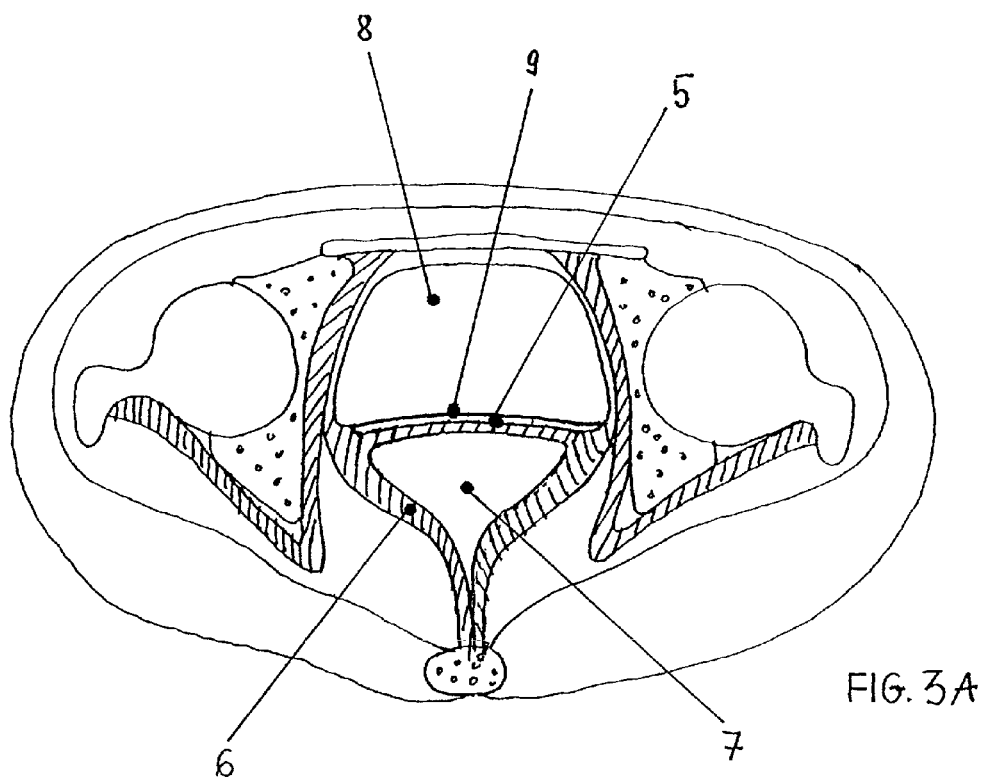
FIGS. 3A and 3B show a simplified transverse section through the female pelvis prior to insertion of a therapeutic device into the vagina (5) (FIG. 3A), and following placement of the therapeutic device (1) inside the vagina (5) above the levator ani muscle (6) (FIG. 3B). Modelling of the posterior wall of the bladder (9) by the device (1) is visible.
Figure 3B:
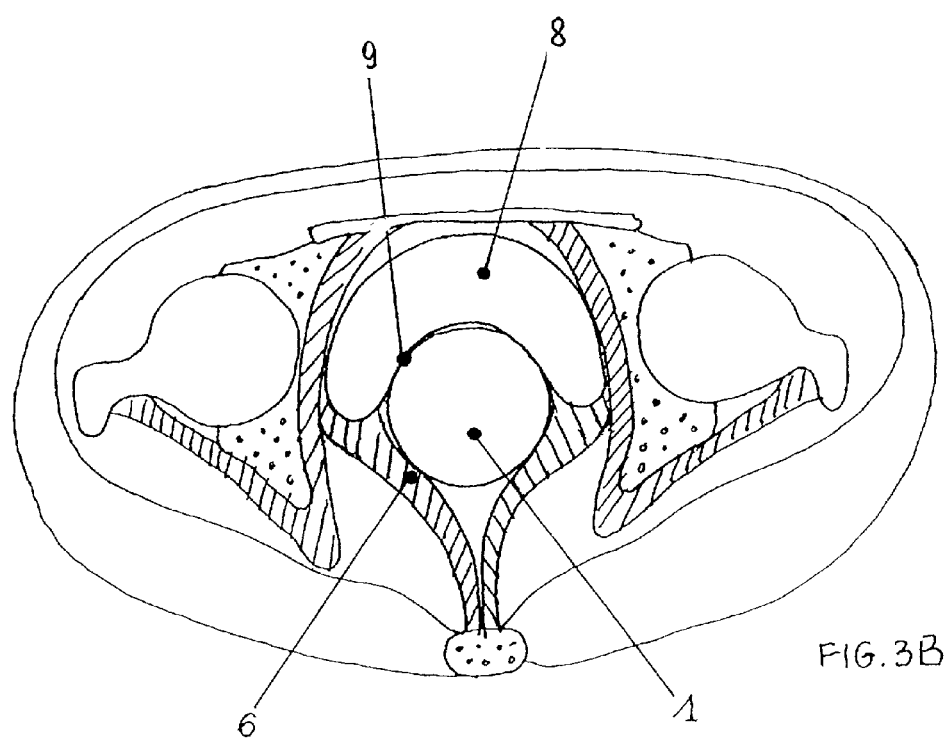
Figure 4A:
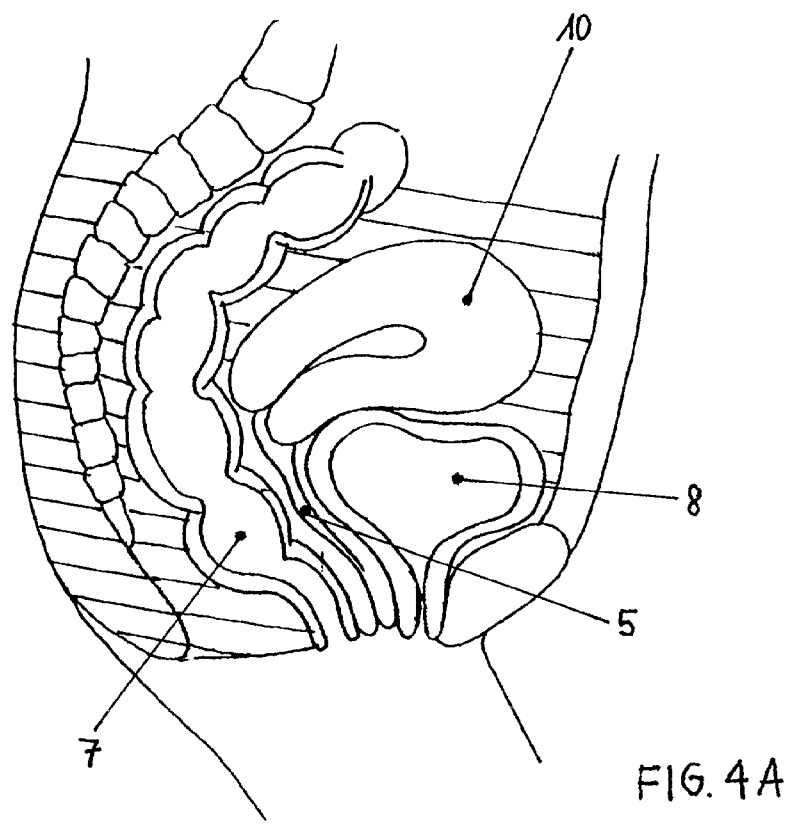
FIGS. 4A and 4B show a simplified sagittal section through the pelvis minor prior to insertion of the therapeutic device (1) into the vagina (5) (FIG. 4A), and following placement of the therapeutic device (1) inside the vagina (5) above the levator ani muscle (6) (FIG. 4B).
Figure 4B:
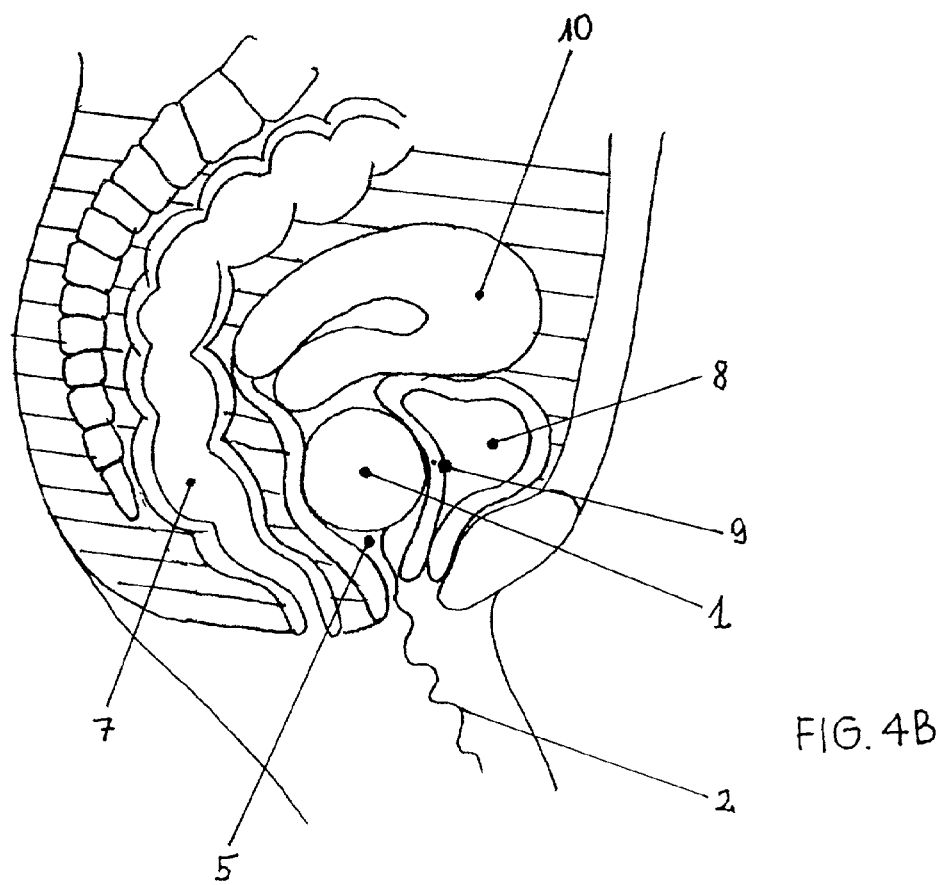

As shown in FIGS. 3B and 4B, the device (sphere) (1), placed in the above mentioned manner inside the vagina (5) above the levator ani muscle (6), models the posterior wall of the urinary bladder (9), simultaneously closing the bladder neck, which most probably reduces sensory hyperactivity originating from receptors located in the urinary bladder neck.

Reduction in urinary urgency is most strongly marked during the night, resulting in alleviation of nocturia (voiding during the night).

While practising the methods of the invention in a patient manifesting symptoms of overactive bladder, appropriate size of a device is selected to fit the vagina of said patient and device is placed in the vagina. The effects are visible instantaneously. Further alleviation of symptoms is observed during the course of continued use of the device.

In case when pelvic floor muscle exercises are performed, the device diameter should be successively reduced.

The devices may be used for an unlimited period of time, including during menstruation. Because of their spherical shape they do not cause ulcer formation.

The use of devices, in accordance with the invention, does not exclude simultaneous administration of pharmacological agents. Concomitant use of the method in accordance with the invention and pharmacological treatment provides a mutually complementary effect.

The present method of treating symptoms of overactive bladder has many advantages in comparison with known pharmacological treatment with anticholinergic agents. Anticholinergic agents act systemically, which results in adverse effects in other parts of the human body, e.g. the circulatory, respiratory, digestive and endocrinologic systems. Because of the mechanism of their action they cause adverse effects that diminish the quality of life, i.e. dry mouth, said effects being the most common cause of therapy discontinuation.

One advantage of the present method is lack of such serious adverse effects. Present method does not have systemic action, reducing detrusor hyperactivity merely by modelling the posterior wall of the urinary bladder by means of a spherical object. A particular advantage is that it can be used in cases where contraindications exist for the use of anticholinergic agents.

Another advantage of the invention is that it may also be used in patients with urinary retention, where such retention is a contraindication to use of anticholinergic agents.

In cases of concomitant overactive bladder symptoms and urinary retention, nonpharmacological treatment in accordance with the invention not only alleviates symptoms of hyperactivity, but also reduces urinary retention.

Description of Clinical Trials

Trials were carried out on 57 women presenting various symptoms of overactive bladder. A device (sphere) was inserted for a period of 6 weeks, after which time the patients were questioned about symptoms of overactive bladder. Urinary urgency subsided in 13 out of 36 patients who complained of this symptom. Continence was achieved in 11 out of 26 patients who complained of urinary urge incontinence. Daytime frequency of voiding in 27 women passing urine more than 8 times per day was reduced from an average of 10.65 SD±3.11 to 6.55 SD±2.69 (statistical significance $p<0.005$). A reduction or alleviation of nocturnal voiding was achieved in 43 women, from an average of 2.10 SD±1.17 to 1.12 SD±1.1 (statistical significance $p<0.005$).

The invention claimed is:

1. A method of treating overactive bladder in women, which comprises:

inserting into the vagina, above the levator ani muscle, an intravaginal device of a spherical hollow ball with no internal movable member therein and of a diameter that fits the width of the vagina, and maintaining said device in the appropriate location inside the vagina for an extended period of time to exert its therapeutic effect.

2. The method according to claim 1, further comprising:

performing pelvic floor exercises including contracting the levator ani muscle and squeezing soft objects placed between the knees while in a prone position with said device remaining inside the vagina.

3. A method of treating overactive bladder in women, which comprises:

inserting into the vagina, above the levator ani muscle, an intravaginal device of substantially spherical shape and a diameter that fits the width of the vagina, and maintaining said device in the appropriate location inside the vagina for an extended period of time to exert its therapeutic effect; and replacing said device with another substantially spherical intravaginal device of a smaller diameter, after strengthening the appropriate muscles and narrowing the width of the vagina.

4. The method according to claim 1, used in combination with pharmacological treatment, in particular by the administration of anticholinergic agents.

5. The method according to claim 1, for the treatment of urinary frequency, nocturia, urinary urgency and/or urinary urge incontinence.

6. The method according to claim 5, for the treatment of urinary frequency.

7. The method according to claim 5, for the treatment of nocturia.

8. The method according to claim 5, for the treatment of urinary urgency.

9. The method according to claim 5, for the treatment of urinary urge incontinence.

10. A method of treating overactive bladder in women, which comprises the steps of:

providing a first set of at least two intravaginal devices each of a spherical hollow ball with no internal movable member therein and of different diameters, designed to be inserted into the vagina and to be left in the vagina in the location above the levator ani muscle for an extended period of time during which a said device of said first set can exert a therapeutic effect, and providing a subset of at least two measuring intravaginal devices of substantially spherical shape and different diameters, said diameters corresponding to the diameters of the devices of the first set, each of said measuring devices having a measuring scale strip attached thereto to determine the location of the measuring device in the vagina;

determining the size and location of a said device of said first set to be left in the body by placing a measuring device of said subset such that the diameter of said measuring device fits the width of the vagina in the appropriate location in the vagina;

removing said measuring device of said subset from the vagina, and inserting a device of substantially spherical shape of said first set having the same diameter as that of the removed measuring device of the subset into the vagina.

11. A method of treating overactive bladder in women, which comprises the steps of:

providing a first set of at least two intravaginal devices of substantially spherical shape and different diameters designed to be inserted into the vagina and to be left in the vagina in the location above the levator ani muscle where a said device of said first set can exert a therapeutic effect, and providing a subset of at least two measuring intravaginal devices of substantially spherical shape and different diameters, said diameters corresponding to the diameters of the devices of the first set, each of said measuring devices having a measuring scale strip attached thereto to determine the location of the measuring device in the vagina;

determining the size and location of a said device of said first set to be left in the body by placing a measuring device of said subset such that the diameter of said measuring device fits the width of the vagina in the appropriate location in the vagina;

removing said measuring device of said subset from the vagina, and inserting a device of substantially spherical shape of said first set having the same diameter as that of the removed measuring device of the subset into the vagina; and removing said device of said first set from the vagina after a period of time and replacing it with another device of said first set of smaller diameter.

12. The method according to claim 11, wherein the following step is included before replacing step as defined above:

determining the appropriate size and location of the device of said first set to be left in the body, by placing said measuring device of a smaller diameter of said the subset in the appropriate location in the vagina.

13. The method according to claim 10, further comprising:

performing pelvic floor exercises consisting in contracting the levator ani muscle and squeezing soft objects between the knees while in a prone position with said device of said first set remaining inside the vagina.

14. The method according to claim 10, further comprising the step of administering pharmacological treatment by the administration of anticholinergic agents.

15. The method according to claim 10, for the treatment of urinary frequency, nocturnal micturition, urinary urgency and/or urinary urge incontinence.

16. The method according to claim 15, for the treatment of urinary frequency.

17. The method according to claim 15, for the treatment of nocturia.

18. The method according to claim 15, for the treatment of urinary urgency.

19. The method according to claim 15, for the treatment of urinary urge incontinence.

* * * * *